(12) United States Patent
Loftman et al.

(10) Patent No.: US 11,844,647 B2
(45) Date of Patent: Dec. 19, 2023

(54) ULTRASOUND CATHETER WITH ADJUSTABLE APERTURES FOR MULTI-PLANE IMAGING

(71) Applicant: Siemens Medical Solutions USA, Inc., Malvern, PA (US)

(72) Inventors: Rickard C. Loftman, Menlo Park, CA (US); William R. Dreschel, State College, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 17/444,777

(22) Filed: Aug. 10, 2021

(65) Prior Publication Data

US 2023/0051315 A1 Feb. 16, 2023

(51) Int. Cl.
*A61B 8/12* (2006.01)
*A61B 8/00* (2006.01)
*A61B 8/14* (2006.01)
*A61B 8/08* (2006.01)

(52) U.S. Cl.
CPC .............. *A61B 8/12* (2013.01); *A61B 8/0883* (2013.01); *A61B 8/145* (2013.01); *A61B 8/445* (2013.01); *A61B 8/4466* (2013.01); *A61B 8/4477* (2013.01); *A61B 8/4494* (2013.01)

(58) Field of Classification Search
CPC ......... A61B 8/12; A61B 8/0883; A61B 8/145; A61B 8/445; A61B 8/4466; A61B 8/4477; A61B 8/4494
See application file for complete search history.

(56) References Cited

U.S. PATENT DOCUMENTS

| | | | |
|---|---|---|---|
| 5,699,805 | A | 12/1997 | Seward et al. |
| 7,500,954 | B2 | 3/2009 | Wilser et al. |
| 7,544,166 | B2 | 6/2009 | Yuan et al. |
| 8,864,675 | B2 | 10/2014 | Dietz et al. |
| 2003/0004439 | A1 | 1/2003 | Pant et al. |
| 2003/0055308 | A1* | 3/2003 | Friemel ............... A61B 8/14 600/15 |
| 2004/0158153 | A1* | 8/2004 | Hirt ..................... A61B 8/12 600/443 |
| 2007/0066902 | A1* | 3/2007 | Wilser ............... B06B 1/0292 600/459 |

(Continued)

FOREIGN PATENT DOCUMENTS

JP 2021502839 2/2021

OTHER PUBLICATIONS

K. Kirk Shung, Diagnostic Ultrasound: Imaging and Blood Flow Measurements, 2015, CRC Press, Second Edition, p. 85 (Year: 2015).*

(Continued)

*Primary Examiner* — Colin T. Sakamoto
*Assistant Examiner* — Tommy T Ly (57) ABSTRACT

For intraluminal ultrasound probes, two long-thin arrays (e.g., 1D arrays) are provided in the intraluminal ultrasound probe for bi-plane imaging. The arrays are rotatable relative to each other so that during insertion the arrays align to be long and thin, allowing the shaft of the probe to be narrow. For bi-plane imaging after insertion, one array is rotated relative to the other array, defining two non-parallel imaging planes.

21 Claims, 5 Drawing Sheets

(56) References Cited

U.S. PATENT DOCUMENTS

| | | | |
|---|---|---|---|
| 2007/0167821 A1* | 7/2007 | Lee | A61B 8/12 |
| | | | 600/463 |
| 2009/0088631 A1 | 4/2009 | Dietz et al. | |
| 2009/0264759 A1* | 10/2009 | Byrd | A61M 25/0136 |
| | | | 600/445 |
| 2009/0265759 A1 | 10/2009 | Ichimi | |
| 2019/0231313 A1* | 8/2019 | Saroha | A61B 8/54 |
| 2021/0177379 A1* | 6/2021 | Kolen | A61B 8/4477 |

OTHER PUBLICATIONS

U.S. Appl. No. 17/303,295, filed May 26, 2021.

* cited by examiner

ULTRASOUND CATHETER WITH ADJUSTABLE APERTURES FOR MULTI-PLANE IMAGING

BACKGROUND

The present embodiments relate to intraluminal ultrasound probes, such as an intracardiac echo (ICE) catheter, or possibly an endocavity probe, trans-esophageal (TEE) probe, or gynecological probe. Intraluminal ultrasound probes typically have a one-dimensional (1D) array for imaging a plane from within the patient. This single plane of information may lead to difficulty in navigation and guidance. Volume imaging may also be provided for providing more information. Due to being on a long, thin probe or shaft for insertion into a lumen, the transducers of intraluminal probes are long and thin. For example, an ICE catheter may have a two-dimensional (2D) array for volume imaging with a long rectangular shape (e.g., 7-23 mm×2-4 mm) to enable vascular access. The quality of imaging in the 2-4 mm dimension is less than for the 7-23 mm dimension and the cost and complexity for the multi-dimensional transducer is much greater than a 1D array.

In many applications, real-time bi-plane imaging provides sufficient spatial anatomic and device position information to support complex structural procedures. TEE and endocavity probes have been implemented with multiple 1D array apertures fixed in orientation to scan different planes or implemented with one rotatable 1D array. These prior devices have not been required to advance through lumens that are too small to support appropriately sized apertures of transverse orientation to the probe/catheter body, such as occurs for ICE applications. While volume imaging capable 2D matrix probes may perform bi-plane imaging, the arrays are extremely complex and typically very expensive compared to more conventional 1D arrays. Imaging resolution transverse to the thin catheter dimension is also very limited to fit in the ICE catheter.

SUMMARY

By way of introduction, the preferred embodiments described below include methods, systems, and improvements for intraluminal ultrasound probes. Two long-thin arrays (e.g., 1D arrays) are provided in the intraluminal ultrasound probe for bi-plane imaging. The arrays are rotatable relative to each other so that during insertion the arrays align to be long and thin, allowing the shaft of the probe to be narrow. For bi-plane imaging after insertion, one array is rotated relative to the other array, defining two non-parallel imaging planes.

In a first aspect, an ultrasound probe is provided for ultrasound. A catheter housing is configured for insertion into a patient. First and second one-dimensional arrays of elements are within the catheter housing. The first one-dimensional array is arranged in-line with the second one-dimensional array along a longitudinal axis of the catheter housing in a first arrangement. The first one-dimensional array is rotatably connected with the second one-dimensional array such that the first and second one-dimensional arrays define different scan planes in a second arrangement.

In a second aspect, an ultrasound imaging system includes an intraluminal ultrasound probe and an ultrasound scanner. The intraluminal ultrasound probe has separate transducer arrays each having a length in azimuth longer than a greatest width of the intraluminal ultrasound probe and a width narrower than the greatest width. The separate transducer arrays are rotatable relative to each other. The ultrasound scanner is configured for bi-planar imaging with the separate transducer arrays. The bi-planar imaging providing images in two non-parallel planes based on the separate transducer arrays being rotated relative to each other.

In a third aspect, a method is provided for ultrasound imaging. An intraluminal probe is inserted into a patient. The intraluminal probe includes at least two transducer arrays positioned with longest dimensions generally parallel to a longitudinal axis of the intraluminal probe. The at least two transducer arrays are rotated relative to each other after the intraluminal probe is inserted into the patient. The at least two transducer arrays as rotated relative to each other are used for imaging in at least two planes defined by the arrays substantially simultaneously.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An endoluminal probe, such as an ICE catheter, has adjustable dual apertures for multi-planar imaging. The ultrasound transducer includes two array segments arranged along a intraluminal body that can be articulated to allow real-time bi-plane imaging, for use in ICE (intra-cardiac echo) and/or endo-cavity interventions. For example, two conventional ultrasound array apertures are physically deployed after insertion, such as in the intra-cardiac space (e.g. atria). In an ICE catheter embodiment, the arrays are sequentially arranged along the catheter for advancing through the vasculature, then a hinge between the arrays allows deploying so that the two imaging planes scannable by the apertures form two planes rotated about the scanning depth dimension. The physical deployment achieves a relative orientation appropriate for bi-plane imaging.

By using two arrays aligned along the longitudinal axis of the probe, the probe maintains the thin probe body. By articulating the arrays relative to each other, two imaging apertures larger than the width of the probe body are provided for multi-planar imaging. Compared to the bi-plane imaging in endo-cavity and TEE transducers with multiple 1D arrays fixed in different orientations, the probe body is configured to allow both arrays to be oriented with the longer azimuthal direction in-line with a single predominant catheter body orientation until the probe is advanced into a space where there is sufficient room to re-orient the arrays for scanning of rotated imaging planes. Compared to probes that achieve different scan plane orientation of a single ultrasound array in sequence, the two arrays allow real-time bi-plane imaging. Both arrays are capable of effectively simultaneous active scanning in frame or line interleaved fashion. Compared to a single volume ICE 2D array, the two 1-D arrays are more cost effective and provide simplicity. The two 1-D arrays can often also provide equivalent lateral resolution in both imaging planes, which similar or same lateral resolution is typically lacking in a single volume ICE 2D arrays due to the size constraint imposed by the catheter body. Matrix arrays for volume imaging may require local active electronics and sophisticated manufacturing techniques whereas two conventional array do not. Conventional 1D ultrasound arrays enable conventional design, manufacture, cost, and complexity.

Bi-plane scanning supports many complex structural procedures and may in fact be preferred to volume imaging. The required navigation and guidance functionality is provided at reduced complexity and cost as compared to using a 2D array. Superior azimuthal resolution in a plane oriented transverse to the predominant probe body axis is provided by articulation of the arrays because azimuthal resolution is directly related to aperture size, which without articulation or deployment is limited by the probe body diameter. The imaging apertures formed by the one-dimensional arrays as deployed for bi-plane imaging have resolutions in azimuth dimensions superior to a resolution of an array limited in size to less than a width of the catheter housing.

Figure 1:
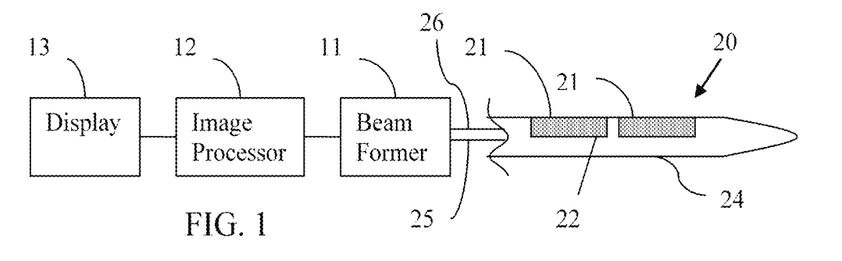
FIG. 1 is a block diagram of one embodiment of an ultrasound system for intraluminal imaging.

FIG. 1 shows an ultrasound imaging system for medical ultrasound imaging with an intraluminal probe 20. The ultrasound imaging system is used for diagnosis and/or treatment. During insertion into the patient, the arrays 21 are mechanically arranged to align in-line along the longitudinal axis of the probe 20. Once in the patient, the intraluminal probe 20 is used for ultrasound imaging using different apertures formed by mechanically rearranging the ultrasound arrays 21. For two arrays 21, bi-plane imaging is provided. Other multi-planar imaging, such as for three or more planes by three or more arrays, may be provided.

The ultrasound imaging system includes the intraluminal probe 20 (e.g., arrays 21 of elements 22 and a housing 24) and an ultrasound scanner (e.g., a beamformer 11, an image processor 12, and a display 13). Additional, different, or fewer components may be provided. For example, the system includes the arrays 21 in an intraluminal probe 20 without the beamformer 11, image processor 12, and/or display 13. The transducer arrays 21 and intraluminal probe 20 releasably connect with the ultrasound scanner or imaging system. As another example, the beamformer 11 and/or image processor 12 may be integrated on a chip or chips with or adjacent to the arrays 21.

The arrays 21 connects to the beamformer 11 by the conductors 25 for imaging. The beamformer 11 includes a plurality of channels for generating transmit waveforms and/or receiving signals. Relative delays and/or apodization focus the transmit waveforms or received signals for forming beams. The beamformer 11 connects with the conductors 25. The beamformer 11 selects one or more apertures including one, some, or all of the elements 22 of a respective one or more of the arrays 21. Different apertures may be used at different times.

The intraluminal probe 20 includes the housing 24, the arrays 21 of elements 22, the conductors 25, and one or more guide wires 26. Additional, different, or fewer components may be provided. For example, a port or tube for inserting and/or withdrawing fluid from the housing 24 is included. As another example, one or more markers for position determination are included.

The electrical conductors 25 connect the elements 22 of the arrays 21 to the beamformer 11. Loose wires and/or flexible circuits with traces connect the electrodes of the elements 22 and/or outputs of subarray beamformers to the conductors 25. Separate connections are provided for separate arrays 21, but multiplexed or shared communications may be used. Alternatively, a daisy-chain approach is used where signals from an end array 21 are passed to the next array 21, and so on until connecting to the conductors 25. The conductors 25 are cables, coaxial cables, traces on flexible circuit material, wires, flex circuits, wire jumpers, combinations thereof, or other now known or later developed conductor. One conductor 16 is provided for each element 24. Alternatively, fewer conductors 25 than elements 22 may be used, such as for switched apertures, partial beamforming, or multiplexing.

The housing 24 is a sleeve of plastic or other material for insertion into a patient. For example, the housing 24 is formed from Pebax. Other materials, such as other Nylons or biologically neutral (or biocompatible) materials, may be used. The housing 24 is sealed over the arrays 21 to separate fluids of the patient from the interior of the probe 20.

The housing 24 is configured for insertion into a patient. In general, the housing 24 is cylindrical in shape, such as a long, thin tube. The housing 24 may be stiff, rigid, flexible, and/or semi-flexible. The housing 24 is shaped and sized to form the insertable portion of the intraluminal probe 20. For example, the housing 24 forms a catheter, TEE, transurethral probe, or endovaginal probe. In one embodiment, the housing 24 forms an ICE catheter with the arrays 21. The arrays 21 may fit within 10 French (3.33 mm), 12.5 French, or another diameter catheter. In another embodiment, the probe 20 and corresponding housing 24 form a micro-TEE for pediatric applications. Examples herein will be for a catheter, but the multiple arrays 21 may be used in various other intraluminal probes 20. The probe 20 is for imaging or for therapeutic application, such as being used to apply high intensity focused ultrasound (HIFU). The images assist in diagnosis, catheter or tool guidance, and/or therapy placement.

Two or more separate arrays 21 are in or on the intraluminal probe 20. The arrays 21 are separate by physical spacing by more than the width of multiple elements 22, by forming separate apertures, and/or by being positionable to scan separate planes. More than two separate arrays 21 may be provided, such as three arrays for multi-planar imaging in three planes. In the examples used herein, bi-plane imaging using two arrays is provided.

Each of the arrays 21 has a plurality of elements 22, backing block, electrodes, and a matching layer. Additional, different, or fewer components may be provided. For example, two or more matching layers are used.

The elements 22 may contain piezoelectric material. Solid or composite piezoelectric materials may be used. Each element is a rectangular solid, cube, or six sided, but other surfaces may be provided. For example, the emitting face of one or more elements 22 is concave or convex for elevation focusing or frequency-based directivity. The elements may be merged into a backing block. Alternatively, a microelectromechanical device, such as a flexible membrane, is used. Any now known or later developed ultrasound transducer may be used.

Any number of elements 22 may be provided, such as ten or hundreds of elements, for each array 21. The elements 22 are adjacent to each other, such as having substantially wavelength or less spacing between the centers of adjacent elements 22.

In one embodiment, each of the arrays 21 is a 1D array. The elements 22 are distributed along a straight or curved line to form the 1D array of elements 22. In other embodiments, one or more of the arrays 21 are 1.5D or 2D arrays. In yet other embodiments, any array having one dimension greater than the width of the probe body and another dimension less than the width may be used to deploy by rotation. For example, a planar imaging array produced as a capacitive micromachined ultrasound transducer (CMUT) where each element is composed of a matrix of micro-elements is used.

Each array 21 is of a same size, shape, and number of elements 22 as another array 21. For example, two arrays 21 are provided. Each array 21 has 64 elements at 110-micron pitch, providing an array length of 7.5 mm along azimuth. The elements 22 and corresponding array 21 have a width along elevation of 1.8-2 mm. Both arrays 21 are sized for imaging at 5 MHz center frequency while fitting within an 8-10 French catheter housing 24. Other arrays 21 may be used, such as with different numbers of elements, element pitches, array lengths, array widths, frequencies of operation, and/or for fitting within different sized housings 24. In alternative embodiments, different arrays 21 have different numbers of elements, sizes, shapes, and/or frequencies of operation from others of the arrays 21. Element count and/or array dimensions may be based on technical limitations or opportunities.

The arrays have elevation widths less than a diameter or width of the probe housing 24. When the azimuth or longitudinal axis of the arrays 21 are aligned with the longitudinal axis of the housing 24, the arrays 21 fit within the housing 24. The azimuth lengths of the arrays 21 are longer than the diameter or width of the housing 24. This sizing where each array 21 has a length in azimuth longer than a greatest width of the intraluminal ultrasound probe 20 of parts positionable within the patient and a width narrower than the greatest width allows the arrays 21 to be aligned along the longitudinal axis of the probe 20 in sequence (see FIG. 1) without requiring the housing 24 to have a larger or expandable size while allowing for higher resolution imaging.

The arrays 21 are positioned distally from the steering section of the housing 24 of the probe 20. Other positions may be provided. The arrays 21 are positioned in-line or sequence along the longitudinal axis within the housing 24 to have a small separation, such as being less than 6 mm apart. In one embodiment, the separation is 2-4 mm. Larger separation than 6 mm may be provided, such as where the bending radius of an articulating region or section 27 is greater.

Figure 2:
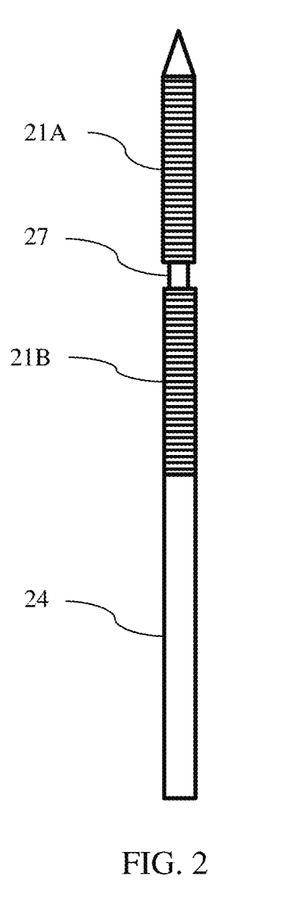
FIG. 2 illustrates one embodiment of a catheter with two arrays aligned for insertion.
Figure 3:
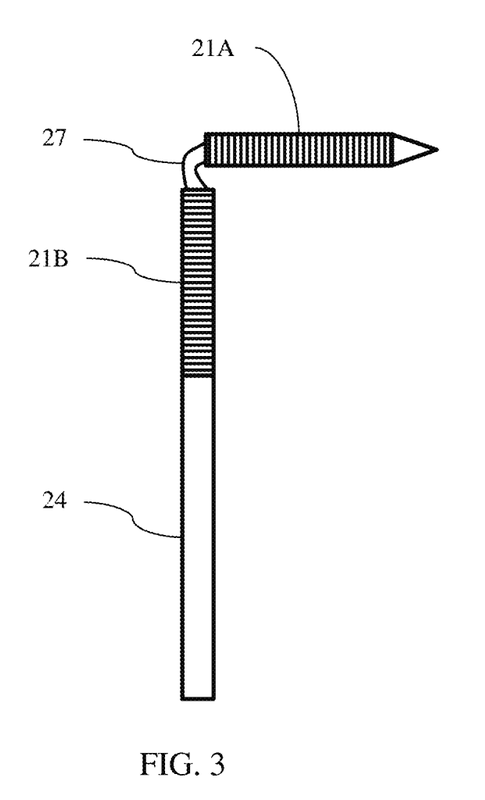
FIG. 3 illustrates the catheter of FIG. 2 with one array rotated relative to the other array for bi-plane imaging.

FIGS. 2 and 3 show an example insertable portion of an ICE catheter having the housing 24, the arrays 21A and 21B, and an articulating section 27. The articulating section 27 is the location where the housing 24 bends to rearrange one array 21A relative to another array 21B. FIG. 2 shows the articulating section 27 while not bent, and FIG. 3 shows the articulating section 27 while bent at 90 degrees. Other angles of bend may be used. The catheter housing 24 may be thinned or its mechanical properties altered at the articulating section 27 to allow for a tight articulation rather than gradual bending, as it is desirable for the two arrays 21A and 21B to be close to one another. The articulating section 27 allows for the housing 24 to be inserted through a lumen in the arrangement of FIG. 2 (i.e., without or with minimal bending between the arrays 21A, 21B) and then bending once inserted to form apertures defining different scan or imaging planes in the arrangement of FIG. 3.

The arrays 21A and 21B are rotatable relative to each other. The rotation occurs at the articulating section 27 between the arrays 21A and 21B. The articulating section 27 bends to allow the relative rotation. The rotation is orthogonal to the catheter body, such as about a depth axis imaged with the array. In the example of FIGS. 2 and 3, the emitting face of the array is shown in the plane of the drawing sheet where an axis orthogonal to the sheet is the depth axis of imaging. Two ultrasound apertures situated are near one another on an intracardiac catheter body distal to the conventional gradually articulating section used for positioning the probe 20. The two ultrasound apertures are rotatable relative to each other with the more sharply articulated section 27 between the arrays 21A and 21B. The articulated section 27 is capable of achieving a relative rotation about the broadside imaging axis of approximately 90 degrees. Other angles may be provided, such as between 10-170 degrees of rotation. The different relative rotations are binary, such as providing only 90-degree rotation. In other embodiments, the amount of rotation may be set or controlled, such as allowing for any intermediate and/or greater rotation positions. Rotation about other axes may be provided.

A hinge connects the two arrays 21A and 21B. The articulating section 27 may act as or be the hinge due to the flexibility of the housing material. In other embodiments, other hinge structures (e.g., plastic or metal hinge) within the housing 24 connect the arrays 21A and 21B for relative rotation.

Figure 4:
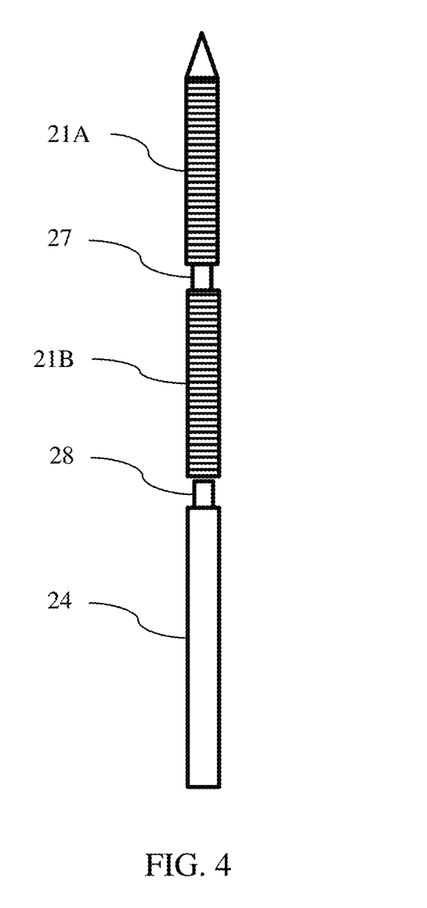
FIG. 4 illustrates another embodiment of a catheter with two arrays aligned for insertion.
Figure 5:
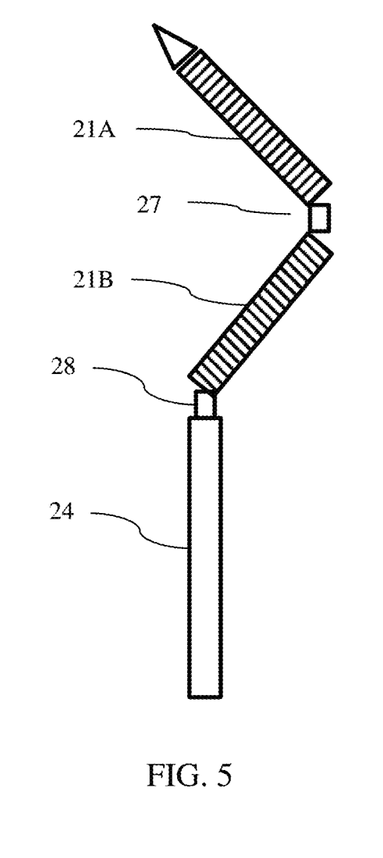
FIG. 5 illustrates the catheter of FIG. 4 with one array rotated relative to the other array and both arrays rotated relative to the longitudinal axis of the catheter for bi-plane imaging.

FIGS. 4 and 5 show another embodiment where an additional articulating section 28 is provided. While the steering capability of the probe 20 may be used to orient the arrays 21A and 21B relative to the patient, the additional articulating section 28 allows for a sharper bend to rotate the arrays 21A, 21B together. This two-hinged approach (i.e., articulating sections 27 and 28) may be used to change the relative rotation of the arrays 21A and 21B with respect to each other (i.e., articulating section 27) as well being used to change the relative rotation of both arrays 21A and 21B together with respect to the probe 20 or longitudinal axis (i.e., articulating section 28). The two-hinged embodiment may be used to change the relative orientation of the two arrays 21A and 21B without regard to maintaining one array 21B along the main catheter body as is used for conventional side fire ultrasound catheters. The articulating section 28 may not be used, maintaining one array 21B along the longitudinal axis or the probe.

Figure 6:
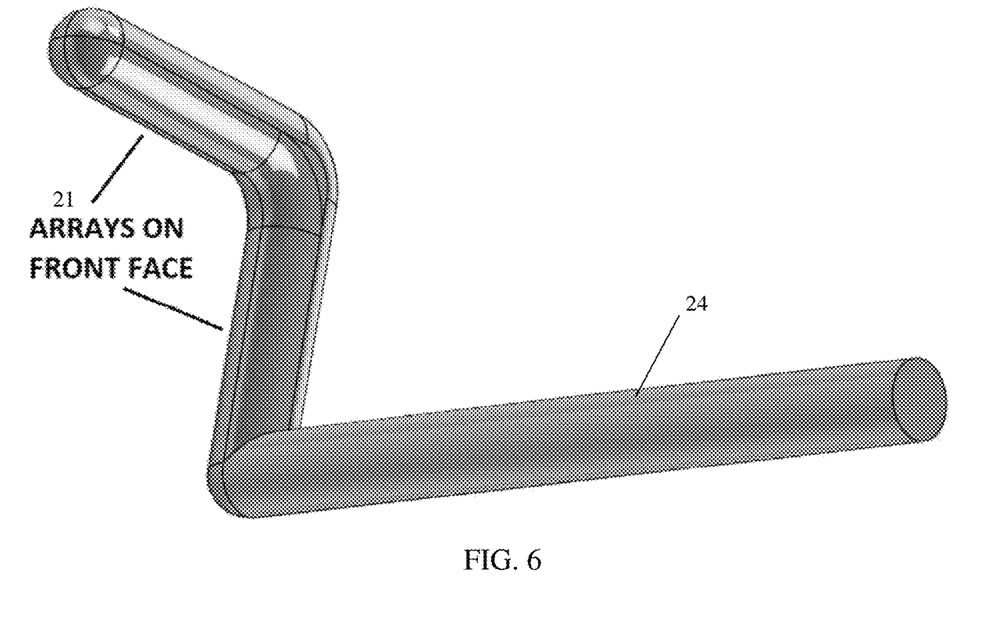
FIG. 6 illustrates another embodiment where rotation of the arrays relative to the longitudinal axis rotates the arrays out of plane.

In the embodiment of FIG. 5, both the articulating sections 27, 28 allow for rotation about the depth axis. The arrays 21A and 21B as well as at least part of the housing 24 are in an azimuth-elevation plane as both bends or rotations are about the depth axis. FIG. 6 shows an alternative embodiment where the articulating section 28 bends or rotates the arrays 21A and 21B out of the azimuth-elevation plane. The separate transducer arrays 21A and 21B are rotatable together relative to an elongated shaft of the intraluminal ultrasound probe 20 where the separate transducer arrays 21A and 21B are rotatable relative to each other in a plane and rotatable together out of the plane. For example, the "L" or "V" arrangement of the arrays 21A and 21B of FIG. 5 may be tilted out of the plane in which the L or V is formed. This might make it easier to position in the heart for certain views of the anatomy within the chamber. A "flashlight" position is provided where one array 21A may be oriented as desired and the other array 21B is oriented relative to that array 21A.

The articulating sections 27 and 28 may limit rotation to be about a single axis. Alternatively, the rotation for one or both hinges may be about more than one axis.

In use, the probe 20 has two or more arrangements of the arrays 21A and 21B relative to each other and/or the longitudinal axis of the probe 20. For example, FIGS. 2 and 4 show in-line arrangements where the arrays 21A and 21B are in line with the longitudinal axis of the probe 20. No or limited bending of the articulating sections 27, 28 is provided so that the catheter housing 24 may be inserted and navigated within the patient. For example, this arrangement is used during insertion and navigation of the catheter through a lumen of the cardiac system of a patient.

FIGS. 3, 5, and 6 show arrangements where one array 21A is rotated relative to the other array 21B. This rotation defines different scan planes, such as perpendicular (e.g., 90-degree rotation) planes or planes at other angles. For example, the catheter is navigated so that the arrays 21A and 21B are within a heart chamber of the patient. Once in the heart, the array 21A is rotated relative to the array 21B to form apertures and corresponding scan planes that are not in a same plane. For example, the array 21A is rotated by 90 degrees to the array 21B about a depth axis, providing orthogonal scan planes. This allows imaging with the different arrays 21A and 21B that provides more spatial information to the viewer. Bi-planar imaging is provided by the bi-planar imaging apertures of the two arrays 21A and 21B.

Since each array provides a distribution of elements 22 in azimuth longer than the width of the housing 24, a greater azimuth resolution than available if restricted to the width of the housing 24 is provided. The bi-planar imaging apertures are longer than a width of the catheter housing 24. Both bi-planar imaging apertures formed by the 1D arrays 21A and 21B have a same resolution in azimuth dimensions. In alternative embodiments, the resolution may be different such as where one array 21A has fewer elements and/or elevation extent than the other array 21B. The long, thin, and flexible form factor of the probe 20 for lumen access can be articulated to achieve two high-quality imaging planes rotated with respect to one another about the depth axis when positioned inside the heart chamber, bladder, etc. Many complex structural heart or other procedures may be accomplished using real-time bi-plane imaging rather than volume imaging. The simpler, potentially less expensive, and higher-image quality implementation using two 1D arrays 21A, 21B as compared to volume imaging from within the probe using a 2D array is achieved with bi-plane imaging rather than a fully-volume capable matrix array.

Figure 7:
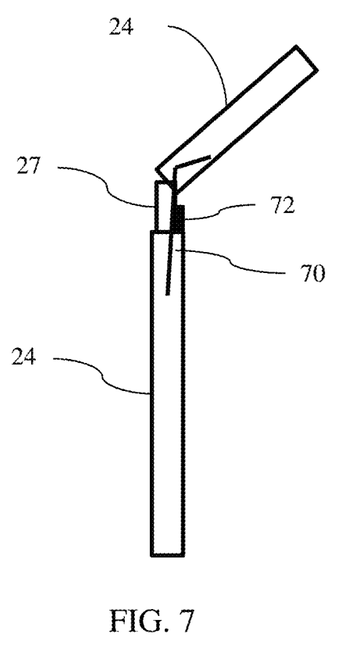
FIG. 7 illustrates a control wire or push rod for articulating one array relative to another.

The arrays 21A, 21B are rotated relative to each other by application of force. Any application may be used. FIG. 7 shows a push rod or guide wire 70 (push and/or pull). For example, an internal or external tether like those used for catheter steering is actuated to pull the distal aperture or array 21A. The rod or wire 70 may be entirely within the housing 24. Alternatively, part of the rod or wire 70 may extend out of the housing 24, such as to allow for angles requiring less force. The rod or wire 70 connects to the array 21B or the housing 24 near the array 21B. Other connection locations may be used. The locations of connection, pulleys, and/or lever arms are used to translate push or pull force to rotation. Gearing or other arrangements may be used. A spring may be included to dispose to a particular amount of rotation (e.g., to apply force to cause the arrangement of FIG. 2 or the arrangement of FIG. 3). The user or a motor (e.g., pneumatic or electrical) may apply the force at the handle of the probe 20.

Figure 8:
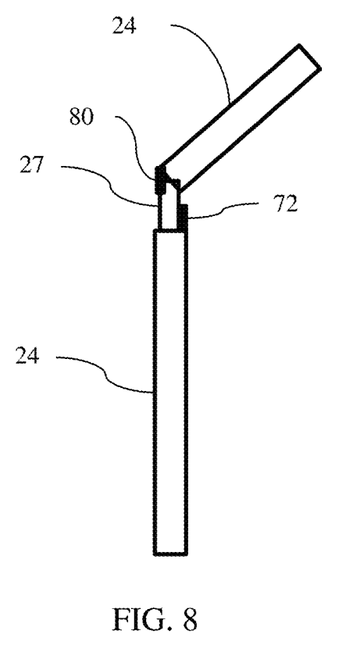
FIG. 8 illustrates a balloon for articulating one array relative to another.

FIG. 8 shows another embodiment where a balloon 80 expands and/or releases to cause rotation. Fluid, such as air or liquid, is pumped into or out of the balloon 80 to cause the rotation at the articulating section 27. In other embodiments, a memory metal is used where heat is applied or not to cause rotation.

Similar or different mechanisms may be used for rotating at the articulating section 28. A spring or other mechanism or redundant device for applying force may be included as a failsafe for one or both articulating sections 27, 28. The probe 20 is disposed to or automatically arranged in the arrangement for insertion (e.g., FIG. 2). If the rotation mechanism fails, then the probe 20 automatically arranges to allow withdraw of the probe 20 from within the patient. This assures easy catheter removal.

FIGS. 7 and 8 show a sensor 72. The sensor 72 senses the amount of rotation (e.g., change in rotation and/or rotation state) of one array 21A relative to the other array 21B. Multiple sensors may be provided. One or more sensors may be provided on the articulating section 28 to sense rotation of the arrays 21A, 21B relative to the probe 20.

Any angle or position sensor may be used. For example, the sensor 72 is a contact sensor. Current, resistive, optical, infrared, magnetic position, Hall effect, GMR, inductive, or capacitive sensors may be used.

Referring again to FIG. 1, the ultrasound scanner (e.g., beamformer 11, image processor 12, and/or display 13) is configured for bi-planar or multi-planar imaging. The separate transducer arrays 21 are used to form separate apertures for different scan planes. The beamformer 11 uses elements 22 of one array 21 to scan a scan or image plane. The beamformer 11 uses elements 22 of the other array 21 to scan a different scan or image plane. For each aperture or array 21, the beamformer 11 electronically focuses along the azimuth direction. A plurality of scan lines using an aperture is scanned. During receive operations, the focus may vary as a function of depth (i.e., dynamic focusing). The scanning using the different arrays is interleaved frame-by-frame, scanline-by-scanline, or by groups of scan lines, providing substantially simultaneous scanning and imaging. Alternatively, separate beamforming and image processing is provided so that the scanning and imaging is simultaneous. Two non-parallel planes are imaged based on the separate arrays 21 being rotated relative to each other.

The image processor 12 is a detector, filter, processor, application specific integrated circuit, field programmable gate array, digital signal processor, control processor, scan converter, three-dimensional image processor, graphics processing unit, analog circuit, digital circuit, or combinations thereof. The image processor 12 receives beamformed data and generates images on the display 13. The images are refreshed on the display 13 at a same time or in an interleaved manner. The imaging is substantially simultaneous. Substantially is used for where the user cannot perceive separate updating, such as updating each of the bi-plane images at 10 Hz or more. Interleaved scanning provides for interleaved imaging, allowing the user to see images of tissue, anatomy, and/or other objects in the fields of view for the two different scan planes at a same time.

Figure 9:
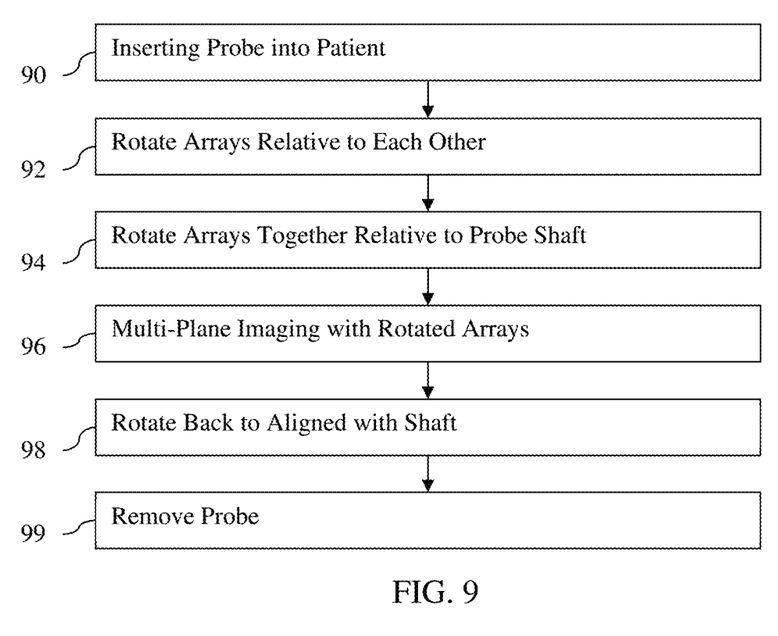
FIG. 9 is a flow chart diagram of one embodiment of a method for ultrasound imaging with a configurable array in an intraluminal probe.

FIG. 9 is a flow chart diagram of one embodiment of a method for ultrasound imaging with an endoluminal ultrasound probe. The probe includes multiple arrays that may be selectively rotated relative to each other, allowing an arrangement for insertion and navigation and a different arrangement for multi-planar imaging.

The probes of FIGS. 1-8 or other intraluminal probes with multiple narrow (narrower than the shaft of the probe) and long (longer than the width of the shaft of the probe) may be used.

Additional, different, or fewer acts may be provided. For example, acts for configuring the ultrasound imaging system and/or acts for diagnosis or treatment are included. As another example, acts 94, 98, and/or 99 are not provided. The acts are performed in the order shown or a different order.

In act 90, the intraluminal probe is inserted into a patient. The probe is inserted into a lumen, such as a blood vessel. For example, the probe is an intra-cardiac catheter inserted into the cardiac system to navigate to the heart.

The intraluminal probe includes at least two arrays. The arrays are separate devices that may be moved relative to each other. The arrays are positioned for insertion in a way that avoids bulges or other interference with the probe moving in the lumen in the patient and/or with the probe entering the patient. For example, the arrays are positioned short-end to short-end, forming a long and narrow arrangement with a width of 3, 5, or 10 mm or less. For other types of probes, the width may be greater, such as 25 mm or less. As another example, transducer arrays are positioned with longest dimensions generally parallel to a longitudinal axis of the intraluminal probe, such as shown in FIGS. 2 and 4.

During insertion and/or navigation, one or more of the arrays may be used to image the patient. The arrays together may be treated as one array due to the in-line alignment along the longitudinal axis (i.e., the imaging aperture extends across the arrays). Only one array is used for imaging by ultrasound during insertion and navigation in other embodiments. Images are generated to assist in insertion. By scanning using the aperture for insertion, two-dimensional images are generated.

In act 92, the transducer arrays are rotated relative to each other. One array may be rotated while maintaining the other array in position to provide relative rotation. Alternatively, both arrays are rotated to provide relative rotation. The rotation rearranges the arrays. The rearrangement forms or defines two different scan planes based on the positions of the arrays.

Force is applied to rotate. The force may release a lock, such as to allow a spring to rotate an array. The force may cause the rotation, such as expanding a balloon, pushing on the more distal array, or pulling on the more distal array.

Once the end of the probe is at the desired location within the patient, such as in the heart, the arrays are rearranged by rotation. The intraluminal probe is bent at the articulating region between the arrays. This bending rotates one array relative to the other.

The rotation is in a plane. For example, the rotation is about a depth axis. FIG. 3 shows an example. The rotation is from the arrangement of FIG. 2 to the arrangement of FIG. 3. The rotation defines a plane in which both arrays as rotated lie. Both arrays share a same azimuth-elevation plane so that rotation about the depth axis keeps the arrays in that azimuth-elevation plane. Other axes of rotation or multiple axes of rotation may be provided.

In act 94, the arrays are rotated together. For example, force is applied to rotate another articulating section, such as shown in FIGS. 4 and 5. The arrays are rotated together relative to a shaft (e.g., part of the shaft of the housing past the steering section and before the proximal most articulating section). The rotation repositions the arrays within the common plane. Alternatively, the rotation repositions the arrays so that at least one of the arrays is no longer in the common plane. FIG. 6 shows an example of rotating the arrays out of the plane.

In act 96, the arrays are rotated are used for imaging. An ultrasound scanner images in the different planes defined by the arrays as rotated relative to each other. The arrays connect with the beamformer to form multiple different apertures for a respective multiple different scan planes, such as orthogonal scan planes for multi-planar imaging. The apertures are used for multi-planar (e.g., bi-plane) scanning. Images of the different planes are generated to assist in diagnosis and/or treatment. By scanning using the apertures, 2D images are generated.

The ultrasound scanner images the different planes substantially simultaneously. "Substantially" allows for line or frame interleaving while providing images for each scan plane at 10 Hz or more. Images for the different planes are generated in real-time. The scanning and/or display for the different arrays may be updated in sequence but the sequence or interleaving is rapid enough to visually provide real-time imaging from all of the arrays of all of the scan planes.

In act 98, the arrays are rotated back to an in-line alignment. This allows for withdraw from the patient. For example, the arrays are rearranged as shown in FIG. 2 or 4. Spring force, force applied by the control wire, or other force rearranges the arrays to return the arrangement used in act 90. In act 99, the probe is removed from the patient.

This bi-planar imaging may assist in interventional applications, such as structural heart applications (e.g., ablation or repair). Other applications include TEE imaging or micro-TEE for pediatric applications or catheter transurethral delivery for bladder imaging (an inflated balloon may be added to helps lock the probe against urethra). For intraluminal probes with sufficient room to have fixed bi-plane arrays, the use of relative rotation instead of fixed arrays may allow reduction in the form factor, such as reducing a maximum width of the insertable portion of an endo-vaginal transducer. The rotatable array arrangement may be used in therapeutic applications, such as where some elements deliver high intensity focused ultrasound and others are used for substantially simultaneous imaging.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ultrasound probe for ultrasound imaging, the ultrasound probe comprising:
a catheter housing configured for insertion into a patient;

a first one-dimensional array of elements within the catheter housing; and a second one-dimensional array of elements within the catheter housing;

wherein the first one-dimensional array is arrangeable in-line with the second one-dimensional array along a longitudinal axis of the catheter housing in a first arrangement, and wherein the first one-dimensional array is rotatable relative to the second one-dimensional array such that the first and second one-dimensional arrays define different scan planes in a second arrangement.

2. The ultrasound probe of claim 1 wherein the first and second one-dimensional arrays have first and second elevation widths less than a diameter of the catheter housing and have first and second azimuth lengths greater than the diameter of the catheter housing.

3. The ultrasound probe of claim 1 wherein the first arrangement is provided during insertion of the catheter housing into a cardiac system of the patient and the second arrangement is provided with the first and second one-dimensional arrays positioned within a heart of the patient.

4. The ultrasound probe of claim 1 wherein the different scan planes of the second arrangement are orthogonal to each other with the first one-dimensional array rotated by 90 degrees from the second one dimensional array about a depth axis of the first one-dimensional array.

5. The ultrasound probe of claim 1 wherein the first and second one-dimensional arrays in the second arrangement provide bi-planar imaging apertures.

6. The ultrasound probe of claim 5 wherein the bi-planar imaging apertures are longer than a width of the catheter housing.

7. The ultrasound probe of claim 5 wherein the bi-planar imaging apertures formed by the first and second one-dimensional arrays have a same resolution in azimuth dimensions.

8. The ultrasound probe of claim 1 wherein a hinge connects the first one-dimensional array with the second one-dimensional array.

9. The ultrasound probe of claim 1 further comprising a wire, rod, or balloon to cause rotation of the second one-dimensional array relative to the first one-dimensional array.

10. The ultrasound probe of claim 1 further comprising a sensor configured to sense an amount of rotation of the first one-dimensional array relative to the second one-dimensional array.

11. The ultrasound probe of claim 1 wherein the first and second one-dimensional arrays are further rotatable together relative to the longitudinal axis of the catheter housing.

12. The ultrasound probe of claim 11 wherein the first and second one-dimensional arrays rotate relative to each other in a first plane and rotate together out of the first plane.

13. The ultrasound probe of claim 1 wherein imaging apertures formed by the first and second one-dimensional arrays in the second arrangement have a resolution in azimuth dimensions superior to a resolution of an array limited in size to less than a width of the catheter housing.

14. An ultrasound imaging system comprising:

an intraluminal ultrasound probe having separate transducer arrays each having a length in azimuth longer than a greatest width of the intraluminal ultrasound probe and a width narrower than the greatest width, the separate transducer arrays rotatable relative to each other; and an ultrasound scanner configured for bi-planar imaging with the separate transducer arrays, the bi-planar imaging providing images in two non-parallel planes based on the separate transducer arrays being rotated relative to each other.

15. The ultrasound imaging system of claim 14 wherein the separate transducer arrays comprise one-dimensional arrays rotatable relative to each other to be in-line and rotatable relative to each other to be at an angle between 10-170 degrees.

16. The ultrasound imaging system of claim 14 wherein the intraluminal ultrasound probe comprises a catheter.

17. The ultrasound imaging system of claim 14 wherein the separate transducer arrays are less than 6 mm apart at an articulating region of the intraluminal ultrasound probe, the relative rotation being at the articulating region.

18. The ultrasound imaging system of claim 14 wherein the separate transducer arrays are rotatable together relative to an elongated shaft of the intraluminal ultrasound probe, the separate transducer arrays rotatable relative to each other in a first plane and rotatable together out of the first plane.

19. A method for ultrasound imaging, the method comprising:

inserting an intraluminal probe into a patient, the intraluminal probe including at least two transducer arrays positioned with longest dimensions generally parallel to a longitudinal axis of the intraluminal probe;

rotating the at least two transducer arrays relative to each other after the intraluminal probe is inserted into the patient; and imaging in at least two planes defined by the at least two transducer arrays as rotated relative to each other substantially simultaneously.

20. The method of claim 19 wherein rotating comprises bending the intraluminal probe in an articulating region between the at least two transducer arrays.

21. The method of claim 19 wherein rotating comprises rotating the at least two transducer arrays relative to each other in a plane common to the at least two transducer arrays, and further comprising rotating the at least two transducer arrays relative to a shaft of the intraluminal probe out of the plane.

* * * * *